(12) United States Patent
Nakazawa

(10) Patent No.: US 9,417,197 B2
(45) Date of Patent: Aug. 16, 2016

(54) METHOD OF MEASURING THICKNESS OF FE—ZN ALLOY PHASE OF GALVANNEALED STEEL SHEET AND APPARATUS FOR MEASURING THE SAME

(71) Applicant: Nippon Steel & Sumitomo Metal Corporation, Tokyo (JP)

(72) Inventor: Makoto Nakazawa, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 70 days.

(21) Appl. No.: 14/380,441

(22) PCT Filed: Apr. 25, 2013

(86) PCT No.: PCT/JP2013/062170
§ 371 (c)(1),
(2) Date: Aug. 22, 2014

(87) PCT Pub. No.: WO2013/161922
PCT Pub. Date: Oct. 31, 2013

(65) Prior Publication Data
US 2015/0055756 A1    Feb. 26, 2015

(30) Foreign Application Priority Data

Apr. 25, 2012   (JP) ................. 2012-099762

(51) Int. Cl.
*G01N 23/207*   (2006.01)
*C23C 2/06*     (2006.01)
(Continued)

(52) U.S. Cl.
CPC ............. *G01N 23/207* (2013.01); *C23C 2/06* (2013.01); *C23C 2/28* (2013.01); *G01B 15/02* (2013.01); *G01N 2223/605* (2013.01); *G01N 2223/633* (2013.01)

(58) Field of Classification Search
CPC ............. G01N 23/207; G01N 23/20; G01N 23/20008; G01N 23/201; G01N 23/20091; G01N 23/223
See application file for complete search history.

(56) References Cited

U.S. PATENT DOCUMENTS 4,064,437 A   12/1977   Hirose et al.
5,155,751 A   10/1992   Chohata et al.
(Continued)

FOREIGN PATENT DOCUMENTS

CN   1392956   1/2003
CN   1800839   7/2006
(Continued)

OTHER PUBLICATIONS

Office Action dated Aug. 5, 2015, issued in corresponding Chinese Application No. 201380002155.2 [with English Translation].
(Continued)

*Primary Examiner* — Hoon Song
(74) *Attorney, Agent, or Firm* — Kenyon & Kenyon LLP

(57) ABSTRACT

A method of measuring a thickness of a Fe—Zn alloy phase included in the Fe—Zn alloy coating of the galvannealed steel sheet includes: an X-ray irradiation process of irradiating the galvannealed steel sheet with the incident X-rays; and an X-ray detection process of detecting the diffracted X-rays obtained in the X-ray irradiation process, derived from a $\Gamma \cdot \Gamma_1$ phase, a $\delta_1$ phase, and a $\zeta$ phase included in the Fe—Zn alloy coating with a crystal lattice spacing d of 1.5 Å or higher.

13 Claims, 12 Drawing Sheets

(51) Int. Cl.
*G01B 15/02* (2006.01)
*C23C 2/28* (2006.01)

(56) References Cited

U.S. PATENT DOCUMENTS

| | | | |
|---|---|---|---|
| 2002/0003858 A1 | 1/2002 | Kondo et al. | |
| 2002/0174918 A1* | 11/2002 | Fujimura | G01N 33/20 148/508 |
| 2006/0140343 A1* | 6/2006 | Gibson | G01N 23/207 378/71 |

FOREIGN PATENT DOCUMENTS

| | | |
|---|---|---|
| CN | 101558454 | 10/2009 |
| EP | 1233265 | 8/2002 |
| JP | 52-021887 | 2/1977 |
| JP | 56-094249 | 7/1981 |
| JP | 58-190747 | 11/1983 |
| JP | 60-058537 | 4/1985 |
| JP | 62-059844 | 3/1987 |
| JP | 01-301155 | 12/1989 |
| JP | 03-249162 | 11/1991 |
| JP | 04-042044 | 2/1992 |
| JP | 04-110644 | 4/1992 |
| JP | 05-045305 | 2/1993 |
| JP | 05-264477 | 10/1993 |
| JP | 06-347247 | 12/1994 |
| JP | 07-260715 | 10/1995 |
| JP | 07-270345 A | 10/1995 |
| JP | 09-033455 | 2/1997 |
| JP | 2001-272358 | 10/2001 |
| JP | 2002-168811 | 6/2002 |
| JP | 3329931 B | 9/2002 |
| JP | 2010-121198 A | 6/2010 |
| JP | 2010-265525 | 11/2010 |
| JP | 2012-255769 | 12/2012 |
| KR | 10-1992-0004832 | 3/1992 |
| KR | 10-19920004832 | 3/1992 |
| KR | 10-2006-0071739 | 6/2006 |
| KR | 10-2007-0031231 | 3/2007 |
| KR | 10-2009-0071208 | 7/2009 |

OTHER PUBLICATIONS

Notice of Allowance dated Aug. 28, 2015, issued in Korean Application No. 10-2014-7000382 [with English Translation].

International Search Report dated Jun. 25, 2013 issued in corresponding PCT Application No. PCT/JP2013/062170 [with English Translation].

International Search Report dated Jan. 14, 2014 issued in PCT Application No. PCT/JP2013/079044 [with English Translation].

Kawabe, Junji et al., "Continuous Measurement of Fe Content in Galvannealed Coating", Kawasaki Steel Technical Report 18, 1986, pp. 129-135 [with English Translation].

European Search Report issued on Nov. 4, 2015 in a corresponding European Application No. 13781069.3.

Akira Taniyama et al: "In-situ Observation of Growth Behavior of Fe—Zn Intermetallic Compounds at Initial Stage of Galvannealing Process", Materials Transactions, vol. 45, No. 7, Jan. 1, 2004, pp. 2326-2331.

Advances in X-Ray Analysis 31, pp. 11-27, issued in 2000 by AGNE Gijutsu Center Inc.

Structural Object vol. 10, No. 1, pp. 20-29, issued in 2004 by AGNE Gijutsu Center Inc.

* cited by examiner

METHOD OF MEASURING THICKNESS OF FE—ZN ALLOY PHASE OF GALVANNEALED STEEL SHEET AND APPARATUS FOR MEASURING THE SAME

TECHNICAL FIELD

The present invention relates to a method of measuring a thickness of a Fe—Zn alloy phase of the galvannealed steel sheet. In addition, the present invention relates to an apparatus used to measure a thickness of a Fe—Zn alloy phase, which can also be used for on-line measurement needed during the manufacture of a galvannealed steel sheet.

This application is a national stage application of International Application No. PCT/JP2013/062170, filed Apr. 25, 2013, which claims priority to Japanese Patent Application No. 2012-099762, filed on Apr. 25, 2012, each of which is incorporated by reference in its entirety.

BACKGROUND ART

A galvannealed steel sheet has been used worldwide as a steel sheet for vehicles. For this application, corrosion resistance, coating properties, weldability, powdering and flaking resistance during press forming, are required for the galvannealed steel sheet. The coating layer of the galvannealed steel sheet includes a $\zeta$ phase, a $\delta_1$ phase, and a $\Gamma \cdot \Gamma_1$ phase. Among the above-described requirements, press formability represented by powdering and flaking resistance is dependent on the amounts of the $\zeta$ phase and the $\Gamma \cdot \Gamma_1$ phase. The powdering resistance is enhanced as the $\Gamma \cdot \Gamma_1$ phase is reduced, and the flaking resistance is enhanced as the $\zeta$ phase is reduced. Therefore, in order to achieve good press formability, a coating layer mainly consists of the $\delta_1$ phase is required.

In order to obtain the coating layer mainly consists of the $\delta_1$ phase, the composition (Al concentration) and the temperature of a coating bath, and heating and cooling conditions for alloying need to be optimized depending on the steel components. In usual operations, the Al concentration and the temperature of a coating bath are maintained within the limited ranges, and a heating and cooling pattern is determined depending on the alloying rate of the steel. However, in practice, due to operational conditions in an upstream process (a process before galvannealing) such as hot rolling, the alloying rate may vary in parts even in the same type of steel and even in the same coil. Therefore, each time, an operator finely adjusts the heating and cooling conditions while visually checking the degree of alloying. The testing of powdering and flaking as well as phase analysis of the coating is performed off-line using the representative parts (typically a front portion and/or a tale portion) of a coil after production.

However, by checking coating quality through the off-line testing and analysis, quick feedback to adjust the operational condition may not be achieved. Therefore, for example, when an alloying rate is changed due to a change in steel type, there is a risk of a reduction in yield. In addition, for example, depending on hot rolling conditions, alloying of the front portion of a coil may be slower than alloying of the middle portion. In this case, when the operation is performed according to the alloying condition of the front portion, the middle portion is excessively alloyed, and it may lead to poor powdering resistance of most of the parts in that coil.

In order to prevent these problems beforehand, on-line measurement with high accuracy over the entire length of the coil is effective. A technique employed for this purpose is an on-line X-ray diffraction. An X-ray diffraction is a method for qualitative and quantitative measurement of crystal phases in a coating layer using the diffraction phenomenon which occurs when crystals are irradiated with X rays with good parallelism. In order to use this method for the on-line measurement, there is a need to select diffracted X-rays having a good correlation with the crystal phase thickness. Furthermore, in order to obtain high measurement accuracy, there is a need to select diffracted X-rays having a high intensity within a practical range of diffraction angle ($2\theta$). In Patent Documents 1 and 2, $2\theta > 80°$, which corresponds to the crystal lattice spacing $d < 1.78$ Å when Cr is used as an X-ray target, is disclosed as a practical range where the effect of vibration and heat radiation of the steel sheet is minor, and the change in incident X-ray intensity is small. As described in Patent Documents 2 to 5, $d=1.26$ Å for a $\zeta$ phase ($2\theta=130°$ when the target is Cr), $d=1.28$ Å for a $\delta_1$ phase ($2\theta=127°$ when the target is Cr), and $d=1.22$ Å for a $\Gamma \cdot \Gamma_1$ phase ($2\theta=139°$ when the target is Cr) are widely used in the previous art.

It is also necessary for the on-line measurement to calibrate the X-ray intensity based on the Zn coating weight, and to adjust the peak angle due to the Fe % in the coating. In addition, it is also important to reduce the effect of vibration of a steel sheet.

One can use different calibration curves between X-ray intensity and the thickness of alloy phase based on the Zn coating weight in order to offset the effect of coating weight (Non-Patent Document 1).

On the other hand, as disclosed in Patent Document 6, by measuring a diffracted X-ray intensity $I_\Gamma$ of a $\Gamma$ phase corresponding to $d=1.22$ Å and a background intensity $I_B$ near a diffracted X-ray position, it is possible to obtain a degree of alloying defined as $(I_\Gamma - I_B)/I_\Gamma$ based on a single calibration curve. In this method, it is assumed that since the effect of the coating weight is reflected on $I_B$, the correction can be achieved.

In Patent Document 5, a method of correcting a change in a diffracted X-ray peak angle due to a change in Fe % in a coating layer is disclosed. Fe—Zn alloy phases have Fe % ranges. $\Gamma$ phase, for example, has a Fe % range of 20 to 28 mass %. Therefore, a crystal lattice spacing changes according to a degree of alloying, and an appropriate diffraction angle $2\theta$ also changes according to the degree of alloying. Patent Document 5 is a technique of, in order to ascertain a change in the diffraction angle $2\theta$, allowing a detector to scan a range of 2 to 5° from $2\theta$ on an arc path. By using this technique, an appropriate range of alloying conditions can be more accurately determined compared to a case where the detector is fixed.

In Patent Document 7, a technique of reducing the effect of vibration of a steel sheet is disclosed. In Patent Document 7, an incident X-ray beam is introduced into a multi-layer optics to be collimated. As a result, diffracted X-rays generated by irradiating the steel sheet with the incident X-ray beam are collimated. Therefore, even when the distance between the detector and the X-rays diffraction position on the steel sheet changes due to vibration, the intensity of the detected X-rays does not change significantly.

PRIOR ART DOCUMENT

Patent Document

[Patent Document 1] Japanese Unexamined Patent Application, First Publication No. S52-21887
[Patent Document 2] Japanese Unexamined Patent Application, First Publication No. H05-45305
[Patent Document 3] Japanese Unexamined Patent Application, First Publication No. H09-33455

[Patent Document 4] Japanese Unexamined Patent Application, First Publication No. H07-260715
[Patent Document 5] Japanese Unexamined Patent Application, First Publication No. H04-110644
[Patent Document 6] Japanese Unexamined Patent Application, First Publication No. H01-301155
[Patent Document 7] Japanese Unexamined Patent Application, First Publication No. 2002-168811
[Patent Document 8] Japanese Unexamined Patent Application, First Publication No. H04-42044
[Patent Document 9] Japanese Unexamined Patent Application, First Publication No. H06-347247

Non-Patent Document

[Non-Patent Document 1] KAWASAKI STEEL GIHO Vol. 18 (1986) No. 2, p. 31

SUMMARY OF THE INVENTION

Problem that the Invention is to Solve

However, the X-ray diffraction according to the related art is not sufficient to perform on-line measurement over the entire coil length with high accuracy, feeding the results back quickly to adjust operational conditions, and to prevent excessive alloying or non-alloying beforehand. The main reason is that the diffracted X-ray peaks derived from the $\zeta$ phase, the $\delta_1$ phase, and the $\Gamma \cdot \Gamma_1$ phase, which have been used from the past, are adjacent to each other and are detected with a strong and irregular background noises.

As a result, for example, as in Patent Document 8, in order to calculate the thickness of three phases, the diffracted X-ray intensity of the phase to be calculated, background intensities at its both ends, and the diffracted X-ray intensities of the other two phases have to be input to a regression equation. In this case, the respective errors are accumulated and thus it is difficult to obtain the thickness of any phase with good accuracy.

In addition, in Patent Document 9, a method to calculate the thickness of each phase using a theoretical X-ray intensity equation having the physical meaning is disclosed. The X-ray diffraction analysis of reference material having a similar diffraction efficiency to a test material is required, as well as the phase analysis according to a constant current electrolysis of the test material. However, in order to obtain the thickness of a single phase, not only the thicknesses of the other phases and the background intensities, but also the diffraction efficiency, the mass absorption coefficient have to be considered, and thus the regression equation becomes extremely complex.

In the related art, it is considered to be important that $2\theta > 80°$, in which vibration of the steel sheet, heat effect of the steel sheet, and the effect of change in incident X-ray intensity are minor. Also it is considered to be important that diffraction peaks of all the three phases (the $\zeta$ phase, the $\delta_1$ phase, and the $\Gamma \cdot \Gamma_1$ phase) are adjacent and are measured simultaneously. As a result, the technique is extremely insufficient to measure the thickness of each phase with good accuracy.

The present invention has been made taking the foregoing problems into consideration. That is, an object of the present invention is to provide a method of measuring a thickness of a Fe—Zn alloy phase included in the Fe—Zn alloy coating of the galvannealed steel sheet, in which the thickness of a Fe—Zn alloy phase can be measured with good accuracy, and an apparatus for measuring the same.

Means for Solving the Problems

The inventors had intensively researched the above object focusing on the lower angle range of $2\theta$ where a background intensity is low and does not fluctuate. As a result, it was found that on a lower angle range corresponding to a crystal lattice spacing d of 1.5 Å or higher, many X-ray diffraction peaks for each phase are present separately. The inventors had thoroughly examined the quantitativeness of the peak intensities, and identified a single peak for each phase, which has the best quantitativeness with a low background intensity. Moreover, the inventors had found that the problem with the measurement accuracy can be solved by using the identified peaks. Furthermore, for simultaneous measurement of more than two phases, it is found to be effective to reduce the asymmetry between the angle of incidence and the angle of reflection for a peak for which highest accuracy is required, thereby completing the present invention.

The present invention has been made on the basis of the findings, and the gist is as follows:

(1) That is, a method of measuring a thickness of a Fe—Zn alloy phase of interest included in the Fe—Zn alloy phase of the galvannealed steel sheet includes: an X-ray irradiation process of irradiating the galvannealed steel sheet with the incident X-rays; and an X-ray detection process of detecting the diffracted X-rays obtained in the X-ray irradiation process, derived from a $\Gamma \cdot \Gamma_1$ phase, a $\delta_1$ phase, and a $\zeta$ phase included in the Fe—Zn alloy phase with a crystal lattice spacing d of 1.5 Å or higher.

(2) In the method of measuring a thickness of a Fe—Zn alloy phase of the galvannealed steel sheet described in (1), in the X-ray detection process, a thickness of the $\Gamma \cdot \Gamma_1$ phase may be measured using a value obtained by subtracting a background intensity from an intensity of the diffracted X-ray derived from the crystal lattice spacing d of 1.914 Å.

(3) In the method of measuring a thickness of a Fe—Zn alloy phase of the galvannealed steel sheet described in (1) or (2), in the X-ray detection process, a thickness of the $\delta_1$ phase may be measured using a value obtained by subtracting a background intensity from an intensity of the diffracted X-ray derived from the $\delta_1$ phase with the crystal lattice spacing d of 2.363 Å.

(4) In the method of measuring a thickness of a Fe—Zn alloy phase of the galvannealed steel sheet described in any one of (1) to (3), in the X-ray detection process, a thickness of the $\zeta$ phase may be measured using a value obtained by subtracting a background intensity from an intensity of the diffracted X-ray derived from the $\zeta$ phase with the crystal lattice spacing d of 4.109 Å.

(5) An apparatus for measuring a thickness of a Fe—Zn alloy phase of the galvannealed steel sheet according to another aspect of the present invention includes: an X-ray tube; and a detector which detects diffracted X-rays from the Fe—Zn alloy phase and measures an intensity of the diffracted X-rays, in which a diffraction angle between a direction of incident X-rays irradiated by the X-ray tube and a direction of the diffracted X-rays detected by the detector is an angle corresponding to a $\Gamma \cdot \Gamma_1$ phase, a $\delta_1$ phase, and a $\zeta$ phase included in the Fe—Zn alloy phase, and with a crystal lattice spacing d of 1.5 Å or higher.

(6) In the apparatus used to measure a thickness of a Fe—Zn alloy phase of the galvannealed steel sheet described in (5), the diffraction angle may be an angle that corresponds to the crystal lattice spacing d of 1.914 Å.

(7) In the apparatus used to measure a thickness of a Fe—Zn alloy phase of the galvannealed steel sheet described in (5) or (6), the diffraction angle may be an angle that corresponds to the crystal lattice spacing d of 2.363 Å.

(8) In the apparatus used to measure a thickness of a Fe—Zn alloy phase of the galvannealed steel sheet described in any one of (5) to (7), the diffraction angle may be an angle that corresponds to the crystal lattice spacing d of 4.109 Å.

(9) In the apparatus used to measure a thickness of a Fe—Zn alloy phase of the galvannealed steel sheet described in any one of (5) to (8), two or more of the detectors may be included, and the diffracted X-rays derived from at least two phases among the $\Gamma \cdot \Gamma_1$ phase, the $\delta_1$ phase, and the $\zeta$ phase may be detected by the detectors.

Effect of the Invention

By applying the method of measuring a thickness of a Fe—Zn alloy phase of interest included in the Fe—Zn alloy phase of the galvannealed steel sheet of the present invention, the thickness of the $\Gamma \cdot \Gamma_1$ phase, the $\delta_1$ phase, and the $\zeta$ phase can be measured with good accuracy without the use of a complex regression equation. In addition, by applying the apparatus for measuring a thickness of a Fe—Zn alloy phase of the galvannealed steel sheet of the present invention, on-line measurement can be performed with high accuracy over the entire coil length. Therefore, by feeding the results back quickly to adjust operational conditions, excessive alloying or non-alloying can be prevented beforehand. This will contribute to improvement of yield and quality assurance. Therefore, a galvannealed steel sheet with excellent coating quality can be stably supplied to customers at low cost.

EMBODIMENT OF THE INVENTION

Figure 1:
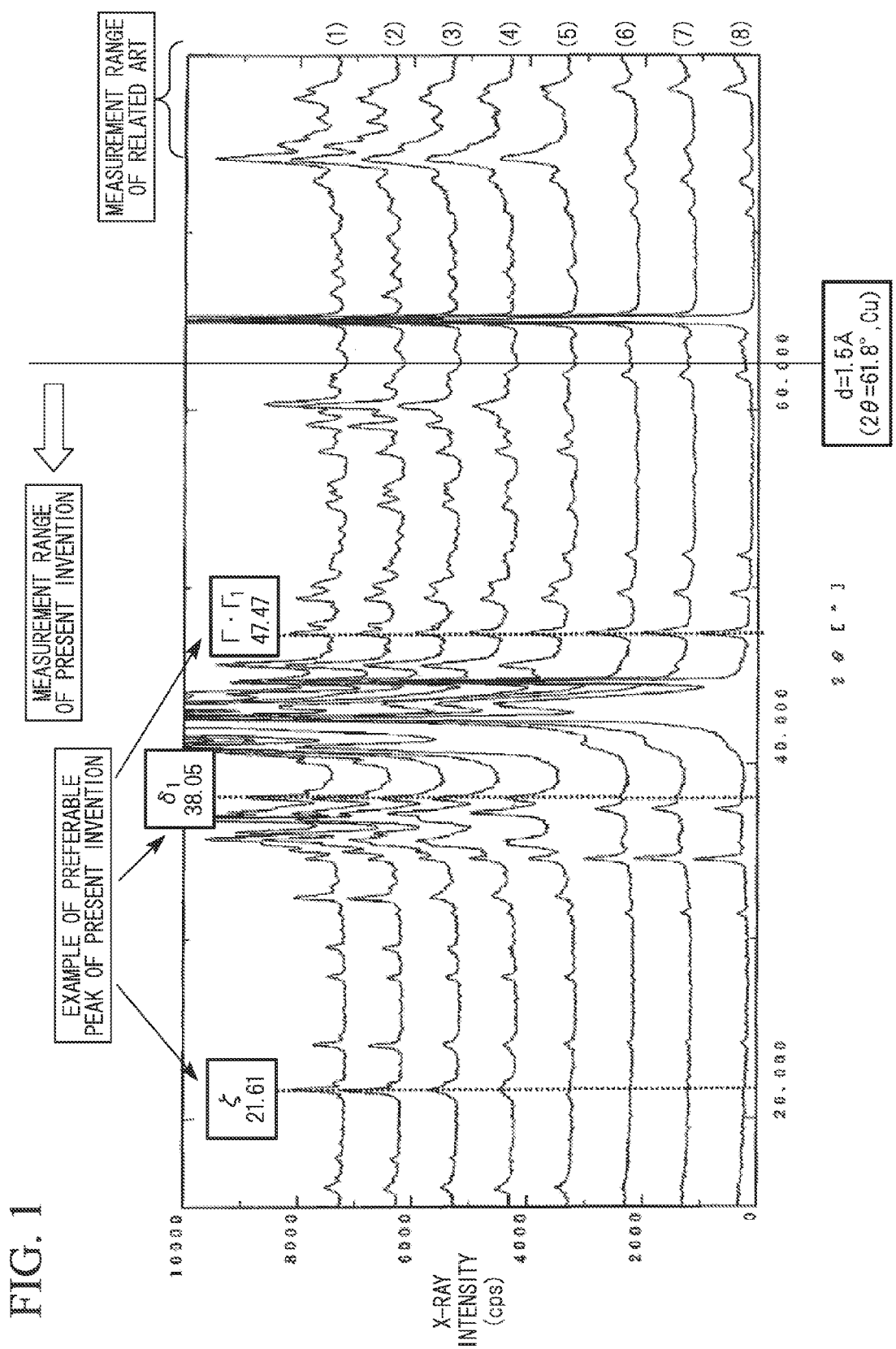
FIG. 1 shows the preferable range of diffraction angles (2θ) and preferable diffraction peaks of each Fe—Zn phase, which are measured in the present invention when Cu is used as an X-ray target.

Hereinafter, a method of measuring a thickness of a Fe—Zn alloy phase included in the Fe—Zn alloy coating of the galvannealed steel sheet according to an embodiment of the present invention (hereinafter, may be simply referred to as a measuring method according to this embodiment) and an apparatus used to measure a thickness of a Fe—Zn alloy phase included in the Fe—Zn alloy coating of the galvannealed steel sheet according to an embodiment of the present invention (hereinafter, may be simply referred to as a measuring apparatus according to this embodiment) will be described in detail with reference to the drawings.

An X-ray diffraction applied to the measuring method according to this embodiment will be described. The X-ray diffraction applied to the measuring method according to this embodiment includes irradiating a polycrystalline specimen with characteristic X-rays and measuring the diffraction intensity at a specific diffraction angle and is classified into the Debye-Scherrer method. In addition, an X-ray diffraction apparatus which can be applied to the measuring method according to this embodiment is constituted by an X-ray generating device which generates an X-ray beam, a slit for restricting the divergence of the X-ray beam, a detector, a slit in front of detector, a count recording device, and the like.

The X-ray generating device which can be used in this embodiment generates X-rays by accelerating the thermal electrons produced by filament current with a high voltage, allowing them to collide with a metal target. The generated X-rays are taken out through a beryllium window. The types of X-ray generating device include a sealed-type X-ray tube and a rotating anode X-ray source. The metal target is selected due to absorption of X-rays by a specimen and measurement accuracy, and Cu, Cr, Fe, Co, Mo, Ti, and the like are used commonly. Among these, Cu and Cr are particularly preferable due to excellent versatility. The generated X-rays include, in addition to Kα rays of interest, Kβ rays and white X-ray components and thus need to be monochromated by removing such components. X-ray beam can be monochromated by inserting a Kβ filter made of a metallic foil in front of the slit or by using a monochromator. Further, a pulse height analyzer may also be combined or a collimation system using an X-ray collimator may also be employed.

For restricting the divergence of the X-ray beam, a solar slit for restricting the divergence in the vertical direction and a divergence slit for restricting the divergence in a horizontal direction is preferably used. Diffracted X-rays generated by irradiating a material surface with the X-ray beam are collected via the light-receiving slit, and, via the solar slit and a scattering slit, are detected by the X-ray detector such that the intensity thereof is measured.

The X-ray detectors which can be used in the measuring apparatus include a scintillation counter, a proportional counter, a semiconductor detector, and the like. Among these, the scintillation counter is the most commonly used. In the measuring apparatus of the present invention, the number of X-ray detectors being used is not particularly limited. For example, when more than two phases are measured, X-ray detectors corresponding to the number of phases of interest and each background may be used.

Next, this embodiment will be described in detail.

First, each of the X-ray diffraction peaks corresponding to each phase to be measured, which is used in the method of measuring a thickness of a Fe—Zn alloy phase according to this embodiment is described. An X-ray diffraction peak corresponding to each phase may be specified using a crystal lattice spacing. The peak has excellent quantitativeness and has a low background intensity, and thus the thickness of each phase can be obtained with good accuracy without the use of a complex regression equation or the like.

The relationship between a diffraction angle ($2\theta$) and a crystal lattice spacing d when Cr or Cu is used as the X-ray target is shown in Table 1. It is characterized in this embodiment that measurement of any alloy phase is performed on a lower diffraction angle compared to the related art. Specifically, in the present invention, measurement is performed at a diffraction angle corresponding to a crystal lattice spacing d of 1.5 Å or higher. A diffraction angle is, as generally defined, twice as large ($2\theta$) as the Bragg angle $\theta$ that satisfies the Bragg diffraction condition for a crystal lattice spacing d. In a range of the diffraction angle corresponding to a crystal lattice spacing d of 1.5 Å or higher, the background intensity in a measured X-ray diffraction spectrum is relatively low. The upper limit of the crystal lattice spacing d does not need to be particularly limited, but is considered to be substantially 6.4 Å or less. As shown in the following Table 1, there are many X-ray diffraction peaks in the range of the diffraction angle corresponding to a crystal lattice spacing d of 1.5 Å or higher, which derived from each of the alloy phases to be focused on. In the following Table 1, the diffraction angles are represented to two decimal places. However, each of the represented diffraction angles is a value calculated from the corresponding crystal lattice spacing d, and in practice, the diffraction angles may be finely adjusted by measuring the intensities of the actual diffracted X-rays. That is, in this embodiment, a diffraction angle ($2\theta$) corresponds to a crystal lattice spacing d means that the diffraction angle includes the diffraction angle ($2\theta$) shown in Table 1 and the angles adjusted within the range of ±0.5°. In addition, in the following Table 1, the coefficient of correlation between the intensity of low angle X-ray diffraction peak and the intensity of main peak of each alloy phase is shown. The correlation coefficient will be described in detail with reference to FIGS. 2A, 2B, 3A, 3B, 4A, 4B, and 4C. The main peak is referred to as an X-ray diffraction peak having the maximum intensity for each alloy phase.

TABLE 1

| No. | Crystal lattice spacing d (Å) | Diffraction angle $2\theta$ (°) Cr target | Diffraction angle $2\theta$ (°) Cu target | Fe—Zn alloy phase | Correlation coefficient | Classification |
|---|---|---|---|---|---|---|
| 1 | 1.507 | 98.95 | 61.48 | ζ | 0.75 | Present embodiment |
| 2 | 1.536 | 96.45 | 60.20 | ζ | 0.72 | |
| 3 | 1.623 | 89.79 | 56.67 | $\delta_1$ | 0.58 | |
| 4 | 1.720 | 83.52 | 53.21 | ζ | 0.65 | |
| 5 | 1.833 | 77.35 | 49.70 | $\Gamma \cdot \Gamma_1$ | 0.90 | |
| 6 | 1.899 | 74.20 | 47.86 | ζ | 0.58 | |
| 7 | 1.914 | 73.49 | 47.47 | $\Gamma \cdot \Gamma_1$ | 0.94 | |
| 8 | 1.971 | 71.07 | 46.01 | $\Gamma \cdot \Gamma_1$ | 0.62 | |
| 9 | 2.363 | 57.97 | 38.05 | $\delta_1$ | 0.77 | |
| 10 | 2.593 | 52.43 | 34.56 | $\Gamma \cdot \Gamma_1$ | 0.90 | |
| 11 | 2.770 | 48.86 | 32.29 | ζ | 0.60 | |
| 12 | 3.692 | 36.15 | 24.09 | ζ | 0.86 | |
| 13 | 4.109 | 32.38 | 21.61 | ζ | 0.98 | |
| 14 | 5.535 | 23.89 | 16.00 | $\delta_1$ | 0.60 | |
| 15 | 6.351 | 20.78 | 13.92 | $\Gamma \cdot \Gamma_1$ | 0.71 | |
| 16 | 1.222 | 139.10 | 78.15 | $\Gamma \cdot \Gamma_1$ | — | Related art |
| 17 | 1.279 | 127.08 | 74.06 | $\delta_1$ | — | |
| 18 | 1.260 | 130.66 | 75.37 | ζ | — | |

In addition, diffraction angles $2\theta$ for obtaining the X-ray diffraction, using variety of targets, derived from a crystal lattice spacing d corresponding to No. 7 of Table 1 are shown in Table 2.

According to Table 2, X-rays targets other than Cr and Cu can also be applied to the measuring method according to this embodiment. Particularly, considering the fact that the apparatus configuration becomes compact as the diffraction angle $2\theta$ is increased, X-ray targets having greater $2\theta$ than Cu are advantageous.

TABLE 2

| X-ray target | Diffraction angle $2\theta$ (°) |
|---|---|
| Sc Kα | 104.76 |
| Ti Kα | 91.84 |
| Cr Kα | 73.49 |
| Fe Kα | 60.90 |
| Co Kα | 55.86 |
| Cu Kα | 47.47 |
| Mo Kα | 21.47 |
| Ag Kα | 16.92 |
| W Kα | 6.53 |

FIG. 1 shows the range of diffraction angles ($2\theta$) of diffracted X-rays derived from each phase used in the measuring method according to this embodiment and the preferable X-ray diffraction peaks of each phase, compared to measurement range of the related art, when Cu is used as the X-ray target. In the related art, in order to measure the thickness of a Fe—Zn alloy phase, the intensities of three adjacent peaks detected with a strong and irregular background noises have been measured. Contrary to this, as shown in FIG. 1, the intensity of a separated peak of each phase with a low background intensity is measured in this embodiment using a lower diffraction angle corresponding to a crystal lattice spacing d of 1.5 Å or higher.

In FIG. 1, eight measurement results of (1) to (8) are superimposed. (1) is a measurement result of galvannealed coating including the $\Gamma \cdot \Gamma_1$ phase, the $\delta_1$ phase, and the ζ phase. On the other hand, (2) to (8) are measurement results of galvannealed coating stripped by a constant potential electrolysis. Electrolytic potentials using a saturated calomel electrode as reference electrode are −1075 mV for (2), −1050 mV for (3), −1040 mV for (4), −1020 mV for (5), −1000 mV for (6), −980 mV for (7), and −940 mV for (8). With changing electrolytic potential from less noble to noble, first, the $\zeta$ phase, and then the $\delta_1$ phase disappear, and only the $\Gamma \cdot \Gamma_1$ phase remains in (8). Even in any of the specimens having different compositions, the three X-ray diffraction peaks ($\zeta$ phase: 21.61°, $\delta_1$ phase: 38.05°, $\Gamma \cdot \Gamma_1$ phase: 47.47°) shown as the preferable examples are characterized in that they can be identified as separated peaks without being affected by the peaks of other phases and backgrounds. It means that when no diffraction peak is detected at these diffraction angles, corresponding phase does not exist in the coating.

Figure 2A:
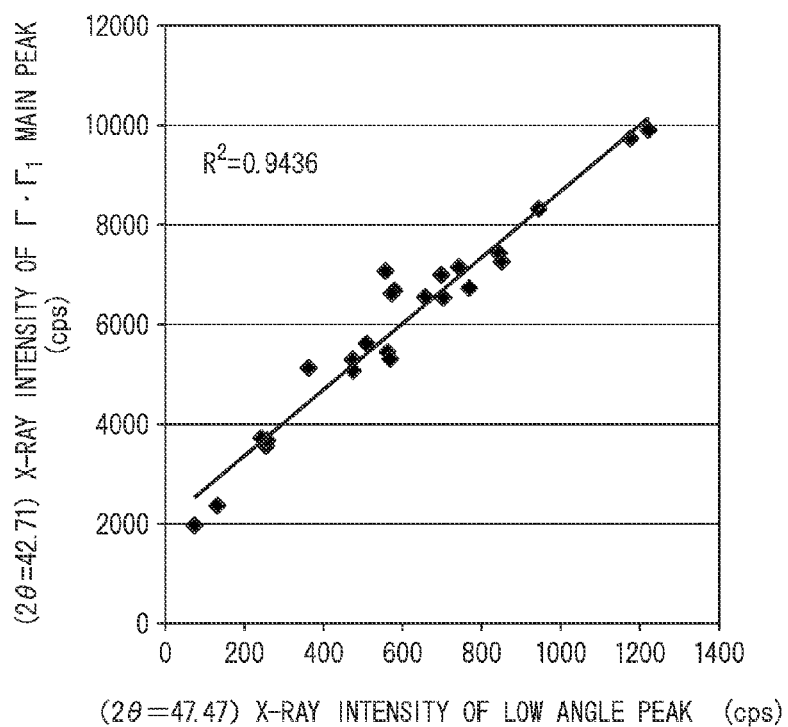
FIG. 2A shows the quantitative relation of low angle X-ray diffraction) (2θ=47.47° of a $\Gamma \cdot \Gamma_1$ phase when Cu is used as the X-ray target.
Figure 2B:
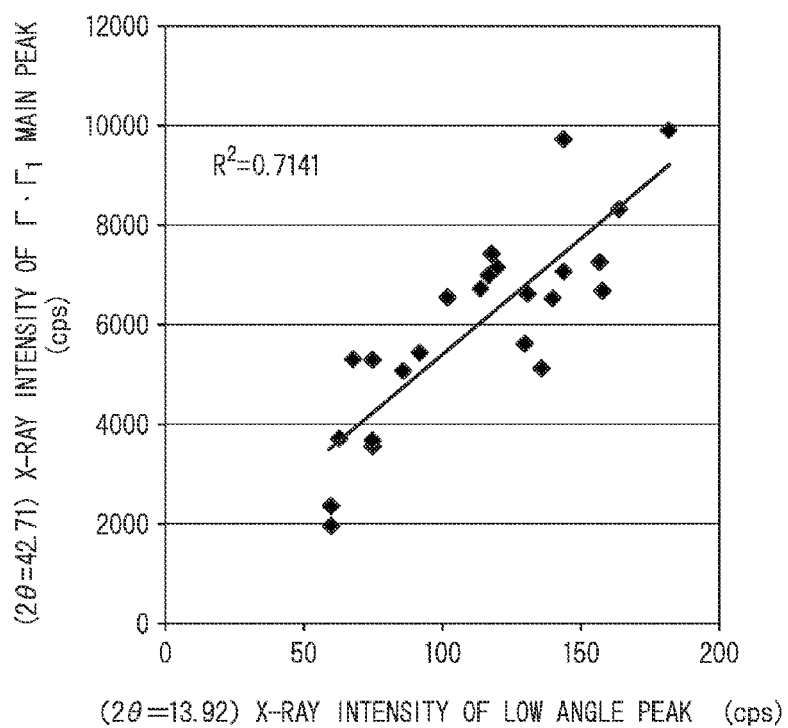
FIG. 2B shows the quantitative relation of low angle X-ray diffraction) (2θ=13.92° of the $\Gamma \cdot \Gamma_1$ phase when Cu is used as the X-ray target.

Next, the quantitativeness of the intensity of the X-ray diffraction peaks corresponding to each phase will be described. The peaks of each phase on a lower angle rage in this embodiment are listed in 1 to 15 of Table 1 with the coefficient of correlation. In FIGS. 2A to 4B, a set of galvannealed steels with different thickness of three phases ($\zeta$ phase, $\delta_1$ phase, and $\Gamma \cdot \Gamma_1$ phase) were analyzed by X-ray diffraction using Cu as the X-ray target, and the intensities of low angle X-ray diffraction peaks and the intensities of main peaks were correlated. FIG. 2A shows the correlation between the intensity of the peak at 2θ=47.47° and the intensity of main peak of the $\Gamma \cdot \Gamma_1$ phase, and FIG. 2B shows the correlation between the intensity of peak at 2θ=13.92° and the intensity of main peak of the $\Gamma \cdot \Gamma_1$ phase. The higher the correlation, the better the quantitativeness of the low angle diffraction peak. The correlation coefficient in FIG. 2A was 0.94, and the correlation coefficient in FIG. 2B was 0.71.

Figures 3A, 3B:
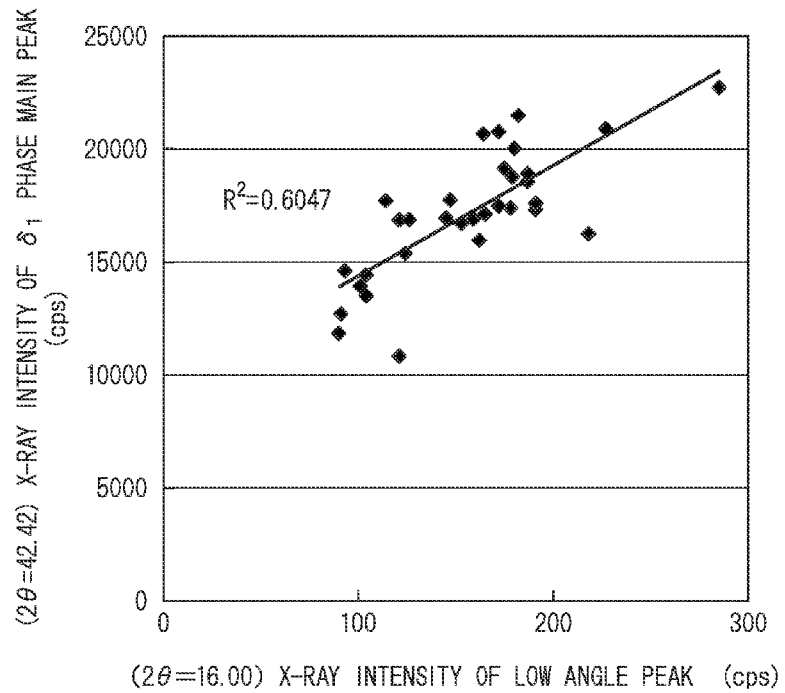
FIG. 3A shows the quantitative relation of low angle X-ray diffraction) (2θ=16.00° of a $\delta_1$ phase when Cu is used as the X-ray target.
FIG. 3B shows the quantitative relation of low angle X-ray diffraction) (2θ=38.05° of the $\delta_1$ phase when Cu is used as the X-ray target.
Figure 4A:
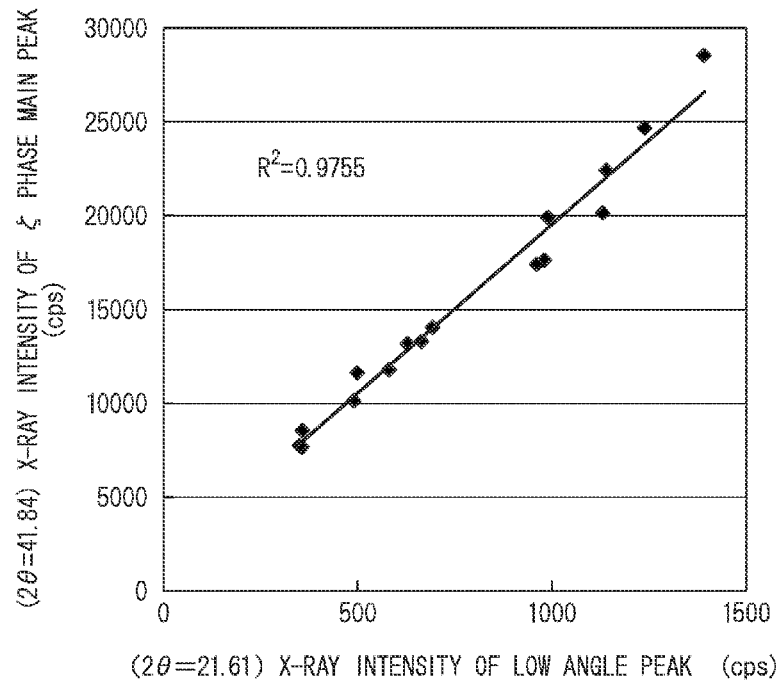
FIG. 4A shows the quantitative relation of low angle X-ray diffraction) (2θ=21.61° of a $\zeta$ phase when Cu is used as the X-ray target.
Figure 4B:
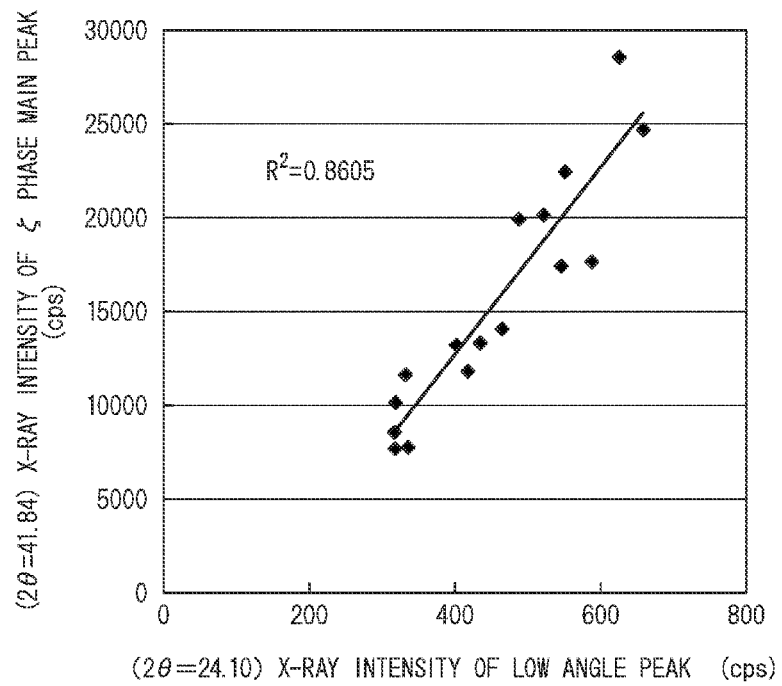
FIG. 4B shows the quantitative relation low angle X-ray diffraction) (2θ=24.10° of the $\zeta$ phase when Cu is used as the X-ray target.
Figure 4C:
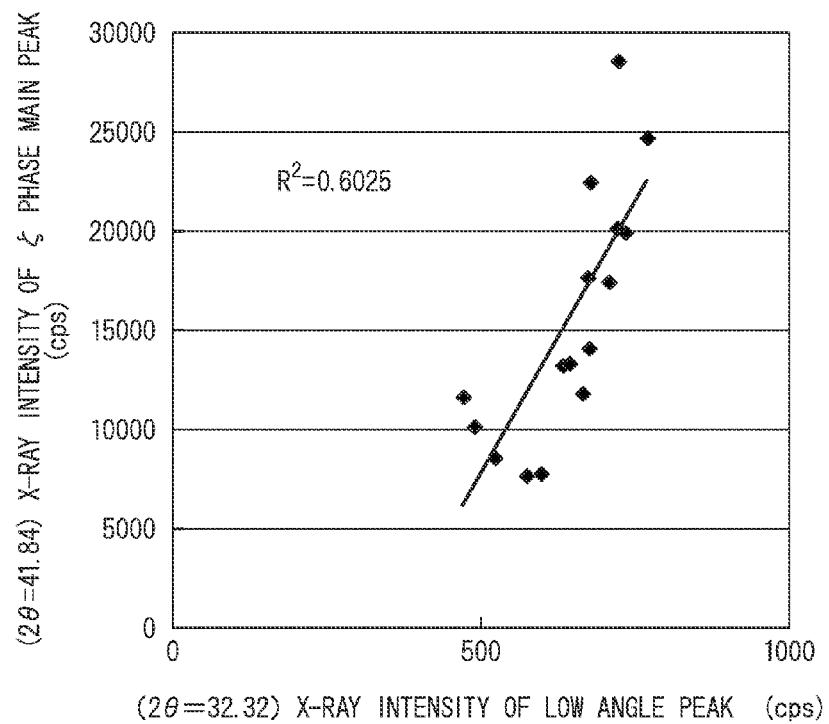
FIG. 4C shows the quantitative relation low angle X-ray diffraction) (2θ=32.32° of the $\zeta$ phase when Cu is used as the X-ray target.

Similarly, FIG. 3A shows the correlation between the intensity of peak at 2θ=16.00° and the intensity of main peak of the $\delta_1$ phase, and FIG. 3B shows the correlation between the intensity of peak at 2θ=38.05° and the intensity of main peak of the $\delta_1$ phase. FIG. 4A shows the correlation between the intensity of peak at 2θ=21.61° and the intensity of main peak of the $\zeta$ phase, FIG. 4B shows the correlation between the intensity of peak at 2θ=24.10° and the intensity of main peak of the $\zeta$ phase, and FIG. 4C shows the correlation between the intensity of peak at 2θ=32.32° and the intensity of main peak of the $\zeta$ phase. The correlation coefficient ($R^2$) is as shown in each FIG and Table 1. It is concluded based on Table 1 that the preferable diffraction peaks shown in FIG. 1 have the best coefficients of correlation among the low angle X-ray diffraction peaks for each phase.

The choice of the low angle X-ray diffraction peaks in this embodiment, however, is not limited to the three preferable peaks shown in FIG. 1. Basically, the X-ray diffraction peaks of the phases shown in Table 1 may be selected with any combination depending on the measurement conditions, although those having higher correlation coefficients shown in Table 1 are preferably selected.

Hereinafter, the measuring apparatus according to this embodiment, that is, an on-line measuring apparatus used to perform measurement of the intensities of the preferable X-ray diffraction peaks corresponding to each phase will be described with reference to FIGS. 5 to 7.

First, the configuration of an apparatus used to measure the thickness of the $\Gamma \cdot \Gamma_1$ phase will be described with reference to FIGS. 5 and 6.

Figure 5:
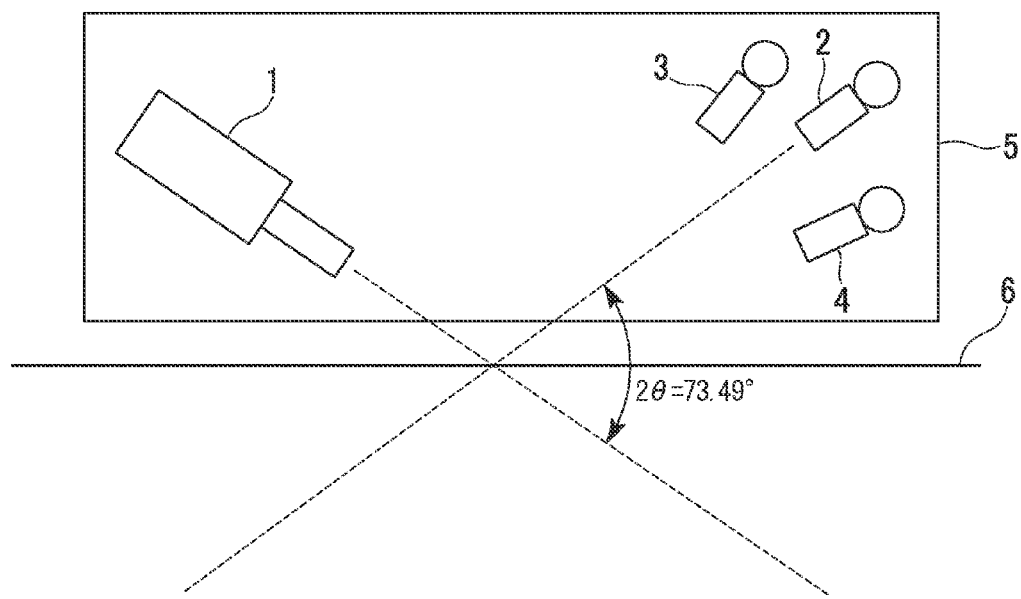
FIG. 5 shows a configuration example of an apparatus for measuring the intensity of low angle X-ray of the $\Gamma \cdot \Gamma_1$ phase according to the present invention when Cr is used as the X-ray target.

FIG. 5 is a schematic diagram of the on-line measuring apparatus which measures the thickness of the $\Gamma \cdot \Gamma_1$ phase when Cr is used as a X-ray target. In FIG. 5, illustration of a slit, a count recording device, and the like is omitted. The incident angle of X-rays is set to 36.75° in order to satisfy the Bragg condition. When a steel strip 6 is irradiated with X-rays from the X-ray tube 1, several diffracted X-rays having different diffraction angles are generated. Among these, a detector 2 measures the intensity of diffracted X-rays derived from the $\Gamma \cdot \Gamma_1$ phase with a crystal lattice spacing of d=1.914 Å. A detector 3 and a detector 4 measure the background intensity on a high angle side and a low angle side respectively. Based on an X-ray diffraction pattern near the diffraction peak corresponding to d=1.914 Å, which is detected by the detector 2, the background measurement angle can be determined, for example, 0.5 to 15° away from the diffraction angle of detector 2. In practice, before the on-line measurement, it is recommended that an appropriate background measurement angle be obtained off-line. The X-ray diffraction peaks in this invention are detected where a background intensity is low, and thus any one of the detector 3 and the detector 4 may be omitted. In addition, when the difference between the diffraction angle and the background measurement angle is 5° or less, it is physically difficult to dispose the detector 3 or the detector 4. Therefore, the diffraction angle of the detector 2 may be scanned within 5° to obtain the background intensity.

The thickness of the $\Gamma \cdot \Gamma_1$ phase can be measured by using the X-ray intensity described above. For example, a value obtained by subtracting the background intensity from the X-ray diffraction intensity may be converted into the phase thickness based on a calibration curve made by a method exemplified in Example 1.

Figure 6:
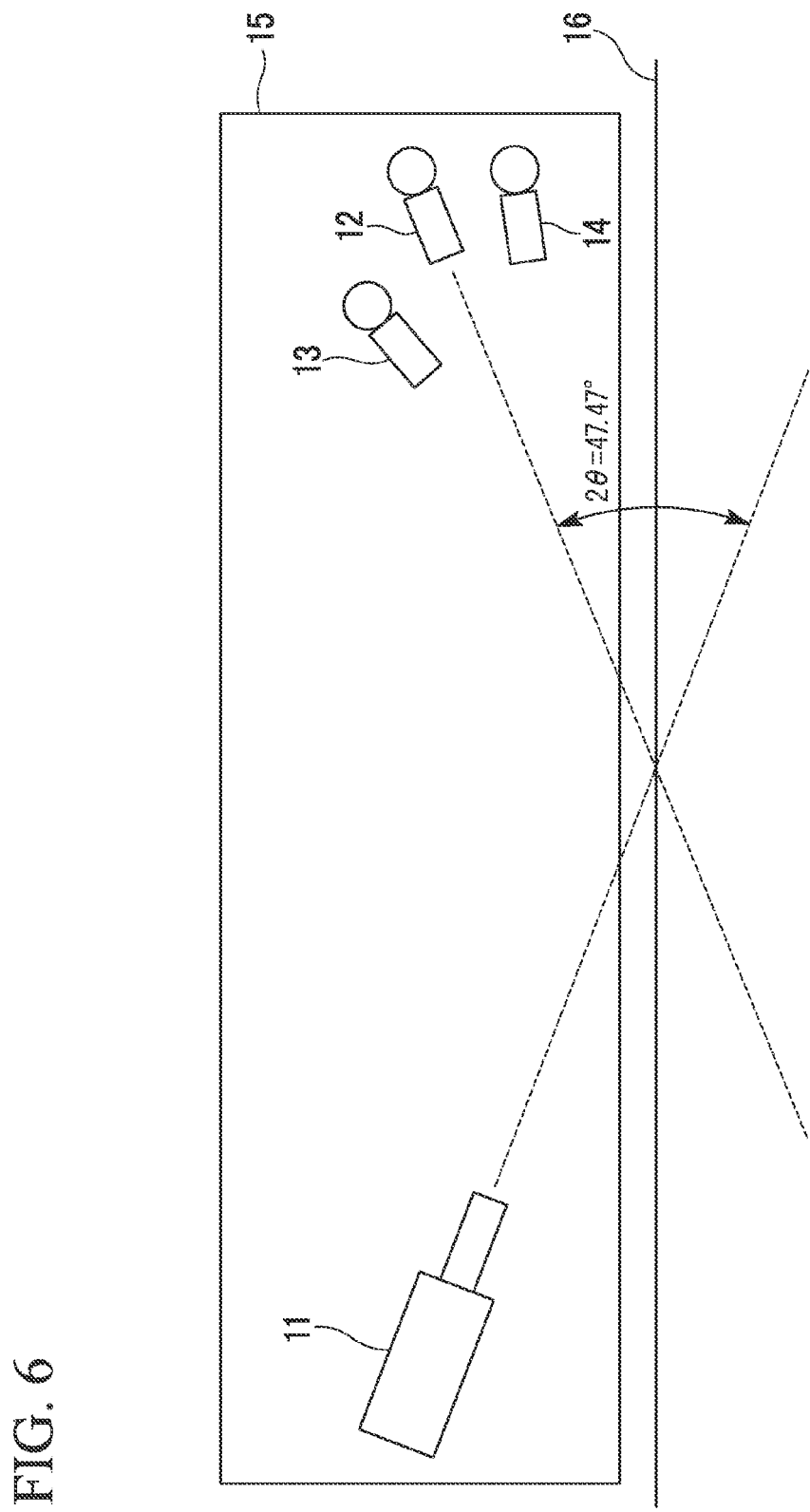
FIG. 6 shows a configuration example of the apparatus for measuring the intensity of low angle X-ray of the $\Gamma \cdot \Gamma_1$ phase according to the present invention when Cr is used as the X-ray target.

FIG. 6 is a schematic diagram of the on-line measuring apparatus which measures the thickness of the $\Gamma \cdot \Gamma_1$ phase when Cu is used as a X-ray target. In FIG. 6, illustration of a slit, a count recording device, and the like is omitted. The incident angle is set to 23.74° in order to satisfy the Bragg condition. A detector 12 measures the intensity of diffracted X-rays derived from the $\Gamma \cdot \Gamma_1$ phase with a crystal lattice spacing of d=1.914 Å. By using the diffracted X-ray intensity, the thickness of the $\Gamma \cdot \Gamma_1$ phase can be measured. A detector 13 and a detector 14 measure the background intensity on a high angle side and on a low angle side respectively. Based on an X-ray diffraction pattern near the X-ray diffraction peak corresponding to d=1.914 Å, which is detected by the detector 12, the background measurement angle can be determined, for example, 0.5 to 15° away from the diffraction angle of detector 12. In practice, before the on-line measurement, it is recommended that an appropriate background measurement angle be obtained off-line. The X-ray diffraction peaks in this invention are detected where a background intensity is low, and thus any one of the detector 13 and the detector 14 may also be omitted. In addition, when the difference between the diffraction angle and the background measurement angle is 5° or less, it is physically difficult to dispose the detector 13 or the detector 14. Therefore, the diffraction angle of the detector 12 may be scanned within 5° to obtain the background intensity.

An apparatus to measure the thickness of the $\delta_1$ phase on-line and an apparatus to measure the thickness of the $\zeta$ phase on-line may be configured similarly to the apparatus illustrated in FIG. 5 or 6. That is, the incident angle θ is set based on the diffraction angles 2θ shown in Table 1, and a diffraction peak corresponding to a crystal lattice spacing d of a phase to be focused on may be detected by a detector.

Figure 7:
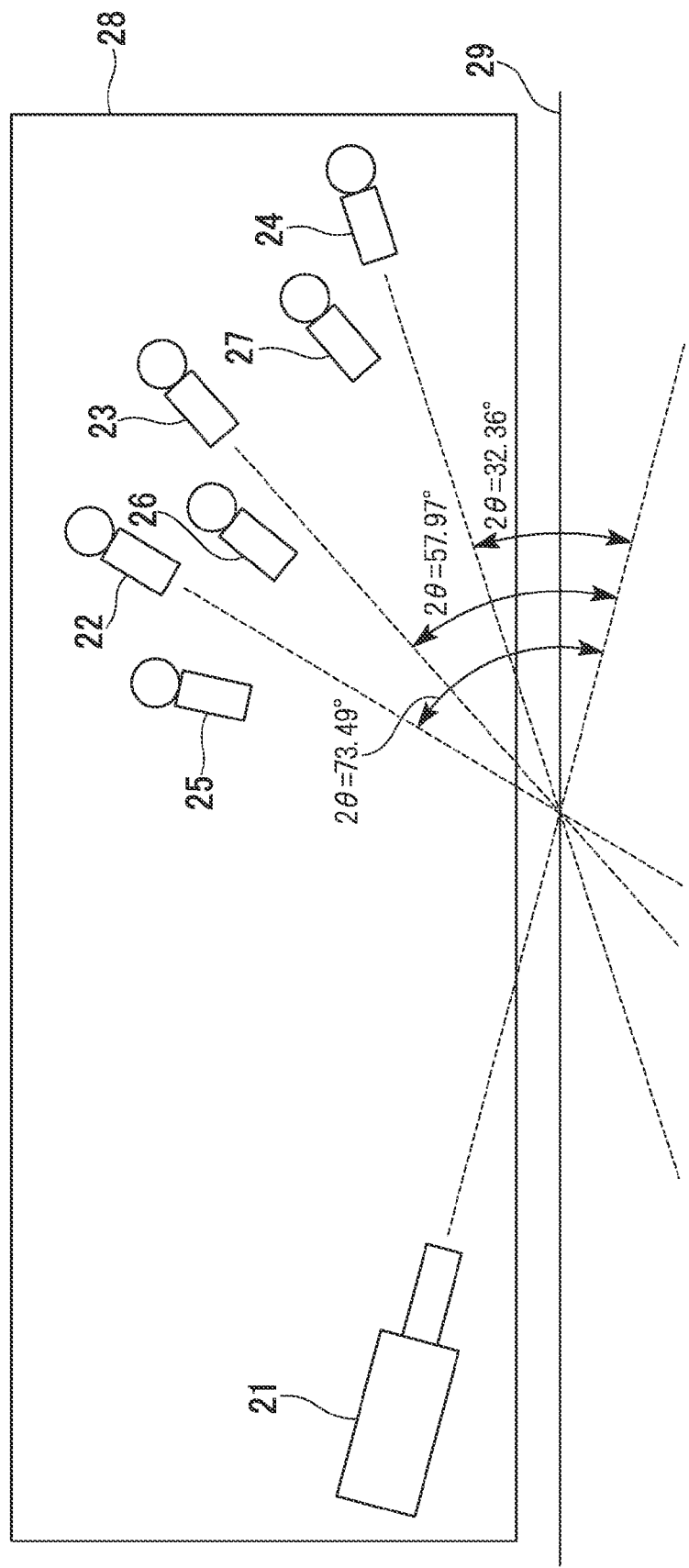
FIG. 7 shows a configuration example of an apparatus for simultaneously measuring the low angle X-ray of the $\Gamma \cdot \Gamma_1$ phase, the $\delta_1$ phase, and the $\zeta$ phase according to the present invention when Cr is used as the X-ray target.

FIG. 7 is a diagram schematically illustrating the configuration of the on-line measuring apparatus for measuring the intensities of diffracted X-rays of more than two phases simultaneously among the $\Gamma \cdot \Gamma_1$ phase, the $\delta_1$ phase, and the $\zeta$ phase which are included in the Fe—Zn alloy.

FIG. 7 illustrates the on-line measuring apparatus for measuring the thicknesses of three phases simultaneously when Cr is used as a X-ray target. The illustration of a slit, a count recording device, and the like is omitted. A detector 22 detects X-ray diffraction peak corresponding to d=1.914 Å of the $\Gamma \cdot \Gamma_1$ phase, a detector 23 detects X-ray diffraction peak corresponding to d=2.363 Å of the $\delta_1$ phase, and a detector 24 detects X-ray diffraction peak corresponding to d=4.109 Å of the $\zeta$ phase. A detector 25 measures the background intensity on a high angle side of the $\Gamma \cdot \Gamma_1$ phase, a detector 26 measures the background intensity on a high angle side of the $\delta_1$ phase, and a detector 27 measures the background intensity on a high angle side of the $\zeta$ phase. In practice, before the on-line measurement, it is recommended that an appropriate background measurement angle be obtained off-line. In FIG. 7, the background intensity is measured only on the high angle side of each X-ray diffraction peak. However, the background intensity can be measured only on a low angle side, or on both the low angle side and the high angle side. In addition, when the difference between the diffraction angle and the background measurement angle is 5° or less, it is physically difficult to dispose the detectors 25, 26, and 27. Therefore, the diffraction angle of the detectors 22, 23, and 24 may be scanned within 5° to obtain the background intensity.

In the measuring apparatus according to this embodiment, the diffraction angles of the three phases are separated from each other as described above, so it is not possible to satisfy the Bragg condition for all the phases at the same time. Even when the Bragg condition is not satisfied, the thickness of the phase can be measured. However, measurement accuracy is increased when the Bragg condition is satisfied. Therefore, it is preferable to determine the incident angle according to the measurement purpose so that the diffracted X-rays derived from the phase whose measurement accuracy is to be maximized satisfy the Bragg condition. In FIG. 7, the incident angle is set to 16.00°. This is because the main purpose is to prevent non-alloying and thus the measurement accuracy of the $\zeta$ phase is considered to be important. On the other hand, when the measurement accuracy of the $\Gamma \cdot \Gamma_1$ phase is considered to be important for the purpose of preventing excessive alloying, the incident angle is preferably set to 36.75°. However, at this incident angle, it is difficult to dispose the detector for the $\zeta$ phase in a head. Therefore, it is preferable that the $\Gamma \cdot \Gamma_1$ phase and the $\delta_1$ phase be simultaneously measured. In this case, the thickness of the $\zeta$ phase can be obtained by subtracting the thicknesses of the $\Gamma \cdot \Gamma_1$ phase and the $\delta_1$ phase from the thickness of the Zn coating weight measured separately. Otherwise, the on-line measuring apparatus for measuring the thickness of the $\zeta$ phase as described above may be used in combination. When only the determination of absence or presence of the $\zeta$ phase is needed, a method of applying a sub-peak (shoulder peak) shown in FIG. 8B, which will be described later, may be used.

In order to offset the effect of the coating weight to the results, obtained by the on-line measuring apparatus as illustrated in FIGS. 5 to 7, it is preferable to use different calibration curves between diffraction X-ray intensity and the thickness of alloy phase based on Zn coating weight. Currently, the coating weight of the galvannealed steel sheet used for vehicles is mainly about 45 g/m$^2$, although those with a coating weight of about 30 g/m$^2$ are also commercialized. For these, different calibration curves are desirably used. When a galvannealed steel sheet having a coating weight of about 60 g/m$^2$ is manufactured, it is desirable to use another calibration curve based on the coating weight.

As a method of correcting a change in a diffraction peak angle due to a change in Fe % in a coating layer, the method described in Patent Document 5 may be applied. In addition, as a technique for reducing an effect of steel sheet vibrations, the method described in Patent Document 7 may be applied.

It has been described how to measure the thicknesses of the Fe—Zn alloy phases on-line by using the apparatuses illustrated in FIGS. 5 to 7. However, the apparatuses illustrated in FIGS. 5 to 7 can also be used for the off-line measurement as well as the on-line measurement.

In the above descriptions, the apparatus uses the three preferable X-ray diffraction peaks. However, the other peaks shown in Table 1 can also be used, by setting the incident angle of X-rays according to the X-ray diffraction angle.

Currently, the manufacturing technique of the galvannealed steel sheet and its coating quality are remarkably advanced and stabilized compared to those at the time when Patent Documents 1 to 9 were filed. For example, variations in the Zn coating weight from a target value are significantly reduced, Fe % in a coating layer does not significantly vary from the target value of 10%, and the coating layer mainly contains the $\delta_1$ phase. Accordingly, a request of customers for coating quality becomes even more strict, and thus slightest powdering or flaking may not be permitted. In the measuring method according to this embodiment, a slight difference in the amount of the $\Gamma \cdot \Gamma_1$ phase or the $\zeta$ phase that slightly remains can be detected with good accuracy. Accordingly, the measuring method according to this embodiment is not a measuring method which is a universal type but has low accuracy, as shown in the related art, in which data is processed by using a complex regression equation to obtain the thickness and the degree of alloying of each phase over a wide range of Zn coating weight and a coating phase configuration. That is, the measuring method according to this embodiment is a measuring method which realizes a precision measurement system, in which a slight difference can be detected with good accuracy in a practically producible range. In addition, the measuring apparatus according to this embodiment is a measuring apparatus which realizes a precision measurement system, in which a slight difference can be detected with good accuracy in a practically producible range.

EXAMPLES

Next, the present invention will be explained using Examples.

In Example 1, the measuring method as described above will be explained. In Example 2, the on-line measurement using the measuring apparatus as described above will be explained. The present invention is not limited to the following examples.

Example 1

Forty samples of galvannealed steel sheet were prepared having different Zn coating weight and different degrees of alloying coated on the different types of steel. Most of the samples were produced in the production line, and a part thereof was prepared in a laboratory. The samples specification is shown as follows.

Types of steel: Nb—Ti sulc, 340BH, and 590DP
Zn coating weight: target values of 45 g/m$^2$ and 30 g/m$^2$
Degree of alloying: Fe (%) of 7.0 to 13.0%

Among these, seven to ten samples having different phase thicknesses were selected, and using these samples, calibration curves were made, showing the relationship between the X-ray intensity of diffraction peaks and the thickness of each phase. Two calibration curves were made in the present invention based on the Zn coating weight and only one calibration curve was made for the related art regardless of the Zn coating weight. The Cr was used as the X-ray target to irradiate the X-rays (Kα rays) at a voltage of 40 kV and a current of 150 mA. The diffraction peaks for the measurement of the present invention and of the related art were both selected from those shown in Table 1. A conventional laboratory X-ray diffractometer was used for the measurement.

Figure 8A:
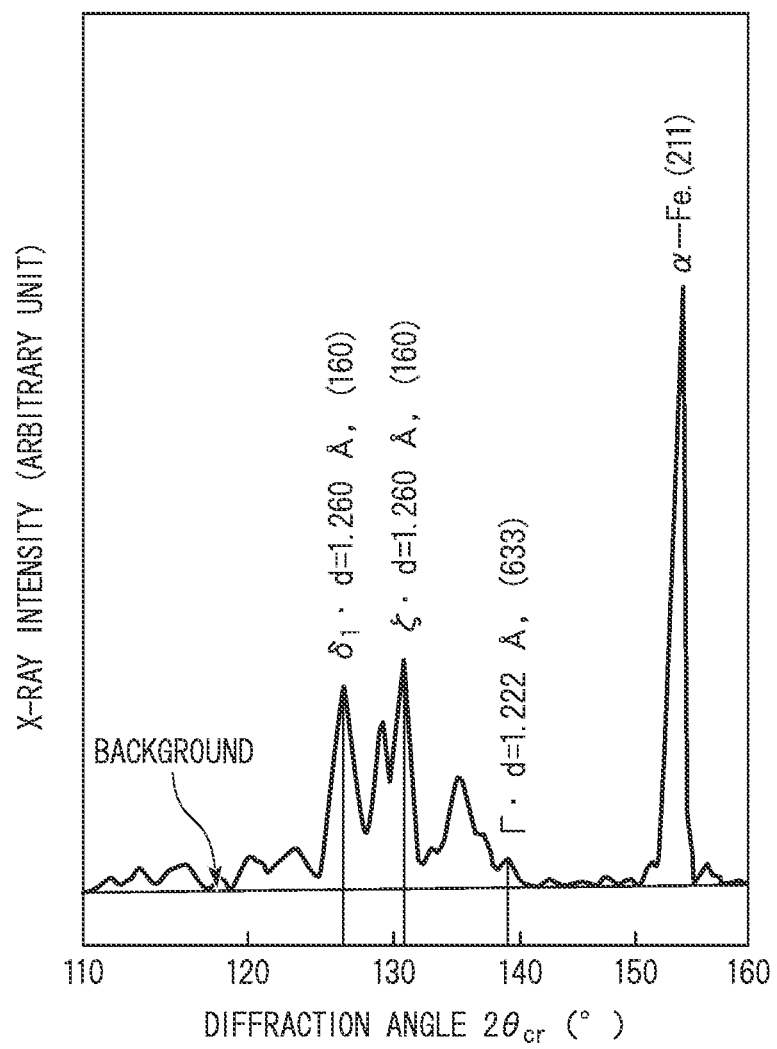
FIG. 8A shows the X-ray diffraction peak of Fe—Zn phases and a background for obtaining the thickness of each Fe—Zn phase simultaneously in the related art.
Figure 8B:
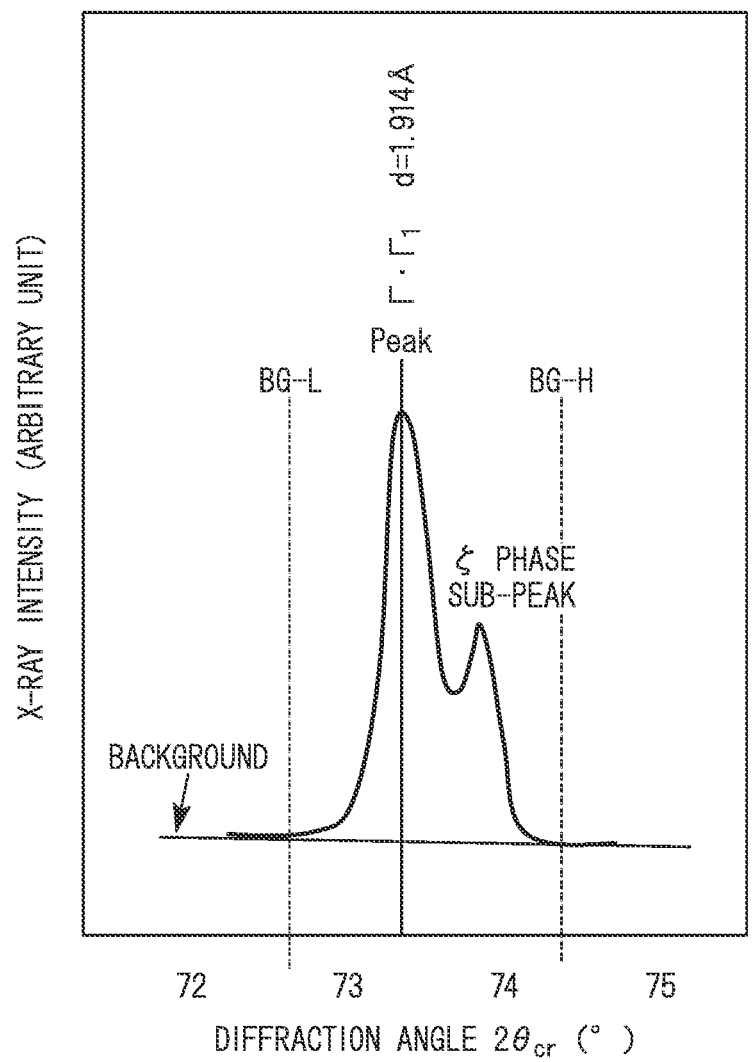
FIG. 8B shows the X-ray diffraction peak and a background for obtaining the thickness of a $\Gamma \cdot \Gamma_1$ phase in the present invention.

FIGS. 8A and 8B show the background setting. For the related art, as illustrated in FIG. 8A, the intensity of a straight line which connects both ends of the entire measurement range including three diffraction peaks was used as the background intensity, according to Patent Document 9. On the other hand, for the present invention, the intensity of a straight line which connects both ends of each diffraction peak is used as the background intensity, as illustrated in FIG. 8B. The shoulder shown on the right of the peak of FIG. 8B is the sub-peak of the ζ phase, and can be used to determine whether the ζ phase is present or not, although its quantitativeness is not sufficient.

The actual thickness of each phase was determined using chemical analysis as follows.

(1) ζ phase: The samples without the η phase (pure Zn phase) and with the ζ phase were chosen by X-ray diffraction analysis. The samples were subjected to constant potential electrolysis at −1030 mV with respect to a saturated calomel electrode, and the disappearance of the ζ phase was checked by X-ray diffraction. The remaining coating weight (g/m$^2$) was measured by chemical analysis (ICP). The difference between this value and the original Zn coating weight (g/m$^2$) was determined as the coating weight (g/m$^2$) of the ζ phase. The thickness (μm) of the ζ phase was calculated by dividing this coating weight (g/m$^2$) of the ζ phase by the specific gravity of the ζ phase, which is 7.15. The relationship between this value (μm) and the intensity (cps) of diffracted X-ray derived from the ζ phase measured before the constant potential electrolysis was determined as the calibration curve of the ζ phase.

(2) Γ·Γ$_1$ phase: The samples without the η phase (pure Zn phase) and without the ζ phase were chosen by X-ray diffraction analysis. The samples were subjected to the constant potential electrolysis at −940 mV with respect to a saturated calomel electrode, and was checked by X-ray diffraction in order to make sure that only the Γ·Γ$_1$ phase remained. The sample was embedded in resin, and was polished for cross-sectional observation, and the average thickness (μm) of the Γ·Γ$_1$ phase was measured by a scanning electron microscope (SEM). The relationship between this value (μm) and the intensity (cps) of the diffracted X-ray derived from the Γ·Γ$_1$ phase measured before the constant potential electrolysis was determined as the calibration curve of the Γ·Γ$_1$ phase.

(3) δ$_1$ phase: The samples without the η phase (pure Zn phase) and without the ζ phase were chosen by X-ray diffraction analysis. A value (g/m$^2$) obtained by multiplying the thickness (μm) of the Γ·Γ$_1$ phase shown in (2) by the specific gravity of 7.36 of the Γ·Γ$_1$ phase was subtracted from the original Zn coating weight (g/m$^2$), and the obtained value was divided by the specific gravity of 7.24 of the δ$_1$ phase to be determined as the thickness (μm) of the δ$_1$ phase. The relationship between this value (μm) and the intensity (cps) of the diffracted X-ray derived from the δ$_1$ phase measured before the constant potential electrolysis was determined as the calibration curve of the δ$_1$ phase. Two calibration curves were made for the δ$_1$ phase. One for the samples with Zn coating weight between 30 and 35 g/m$^2$ and one for the samples with Zn coating weight between 45 and 55 g/m$^2$.

Next, using the remaining samples, the correlation between a thickness (μm) estimated from the measurement value (cps) of the diffracted X-ray intensity by using the calibration curve and an actual measurement value (μm) of a film thickness (μm) obtained by chemical analysis described above was examined. A conventional laboratory X-ray diffractometer was used for the measurement.

Figure 9A:
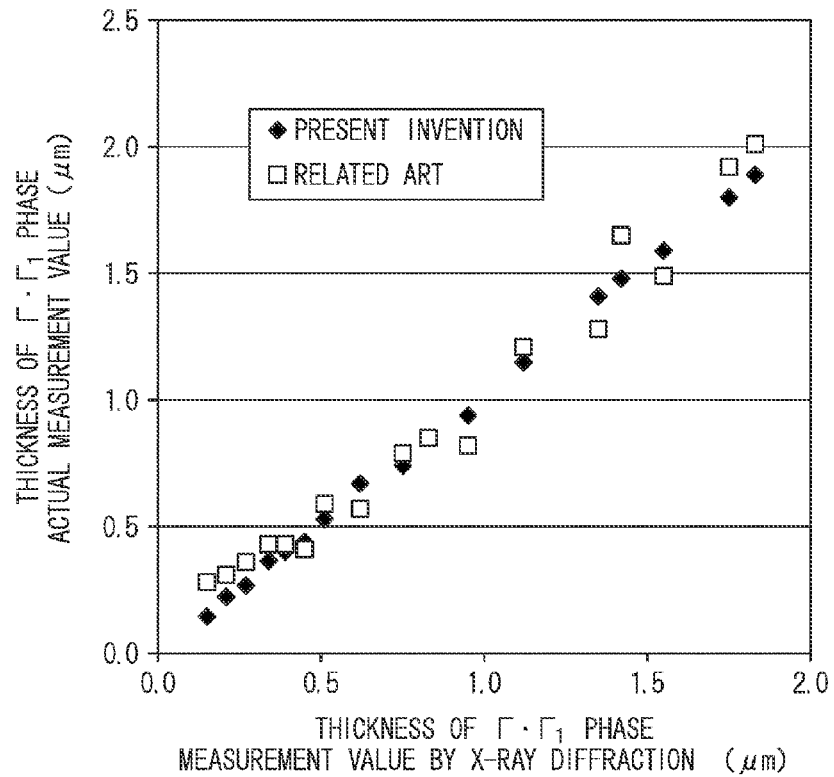
FIG. 9A shows the correlation between the thickness of the $\Gamma \cdot \Gamma_1$ phase measured by X-ray diffraction and the thickness measured by chemical analysis.
Figure 9B:
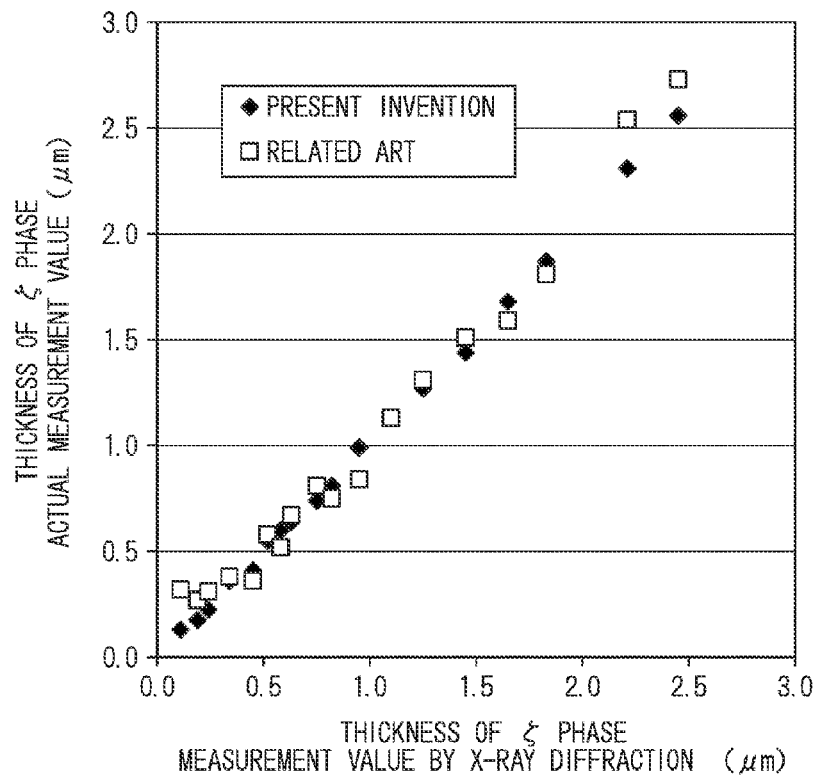
FIG. 9B shows the correlation between the thickness of the $\zeta$ phase measured by X-ray diffraction and the thickness measured by chemical analysis.
Figure 10A:
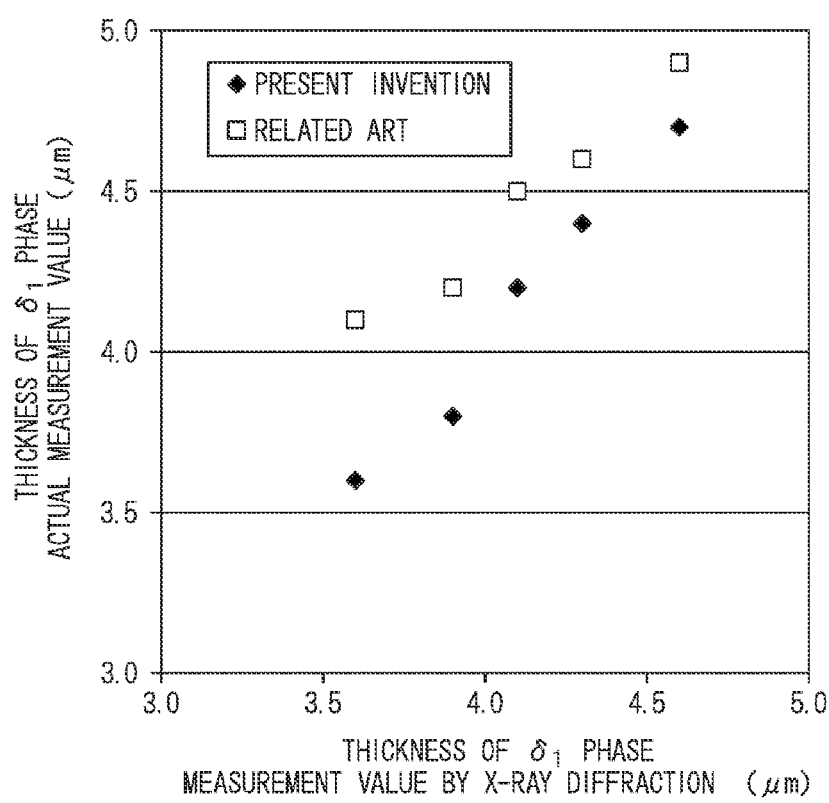
FIG. 10A shows the correlation between the thickness of the $\delta_1$ phase measured by X-ray diffraction and the thickness measured by chemical analysis, when Zn coating weight is around 30 g/m².
Figure 10B:
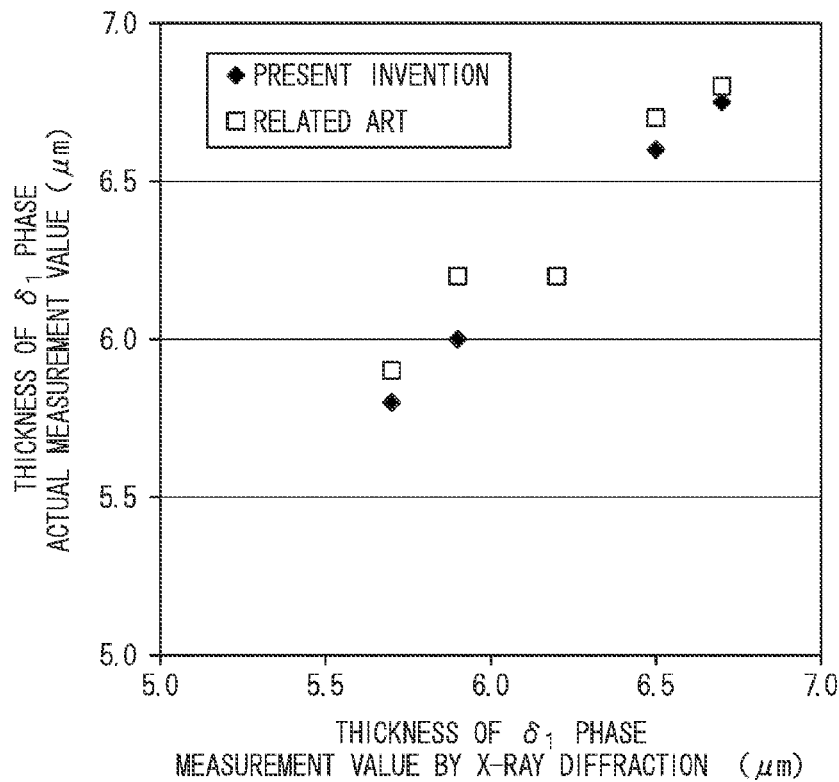
FIG. 10B shows the correlation between the thickness of the $\delta_1$ phase measured by X-ray diffraction and the thickness measured by chemical analysis, when Zn coating weight is around 45 g/m².

The results are shown in FIGS. 9A, 9B, 10A, and 10B. FIG. 9A shows the result of the Γ·Γ$_1$ phase, FIG. 9B shows the result of the ζ phase, and FIGS. 10A and 10B show the results of the δ$_1$ phase. For the present invention, the calibration curves used in FIGS. 10A and 10B are different.

It can be seen from FIGS. 9A, 9B, 10A, and 10B that the correlation of the present invention is better than that in the related art. Particularly, regarding the δ$_1$ phase, good correlations are obtained for both FIGS. 10A and 10B of the present invention, in which two calibration curves are made according to the Zn coating weight. On the other hand, in the related art in which only one calibration curve is made regardless of the Zn coating weight, there is a large gap, especially with the lower coating weight range in FIG. 10A.

Example 2

In the continuous galvanizing line, a coil of steel sheet was galvannealed changing the heating temperature and the line speed, and the thickness of the Γ·Γ$_1$ phase was continuously measured on-line. The measuring apparatus used to measure the diffracted X-ray intensity is the apparatus having the structure illustrated in FIG. 6. Three coils were prepared. The first coil was a dummy coil for setting operational conditions. The second coil (steel type: 340BH) and the third coil (steel type: Nb—Ti sulc) were galvannealed continuously, in order to see if a change in the thickness of the Γ·Γ$_1$ phase according to a change in the operational conditions could be monitored on-line. The coating bath composition was Zn-0.138% Al-0.03% Fe, and the bath temperature and the sheet temperature inserted into the coating bath were 460° C. In order to evaluate the validity of the measurement results, samples were collected from the front portion and the tail portion of the coil subjected to the on-line measurement, and a coating adhesion test was performed by a U bead method.

Figure 11:
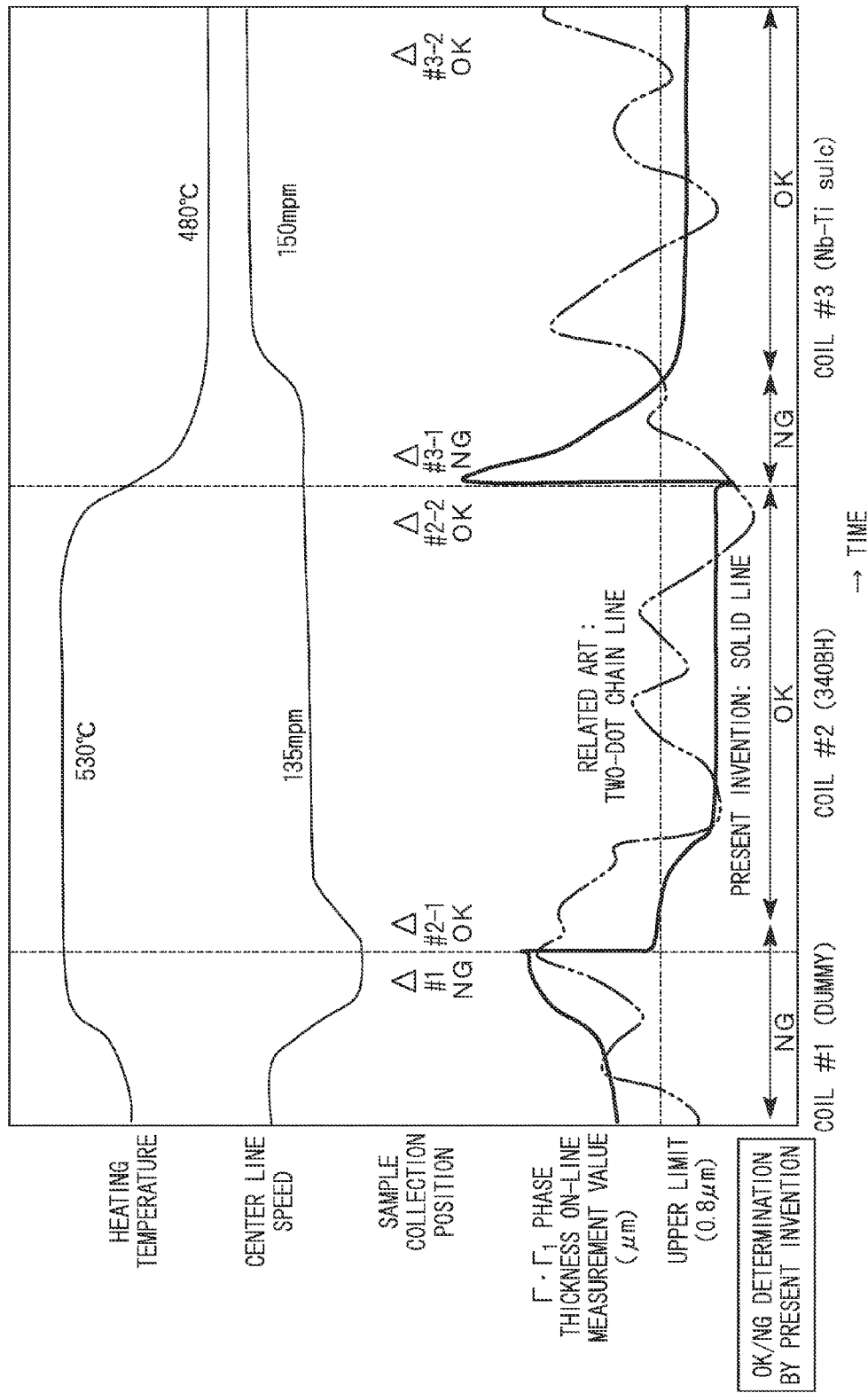
FIG. 11 shows the thickness of $\Gamma \cdot \Gamma_1$ phase measured by on-line continuous X-ray diffraction when a coil is passed through the CGL (continuous galvanizing line) with changing line speed and heating temperature.

The results are shown in FIG. 11. The horizontal axis represents time, and the coil #1 (dummy), the coil #2 (340BH), and the coil #3 (Nb—Ti) were continuously galvannealed.

The upper two curves show changes in a heating temperature and a line speed in an alloying furnace of the CGL, which are the operational conditions, as a function of time. As can be seen from FIG. 11, at the time of a transition from the dummy coil #1 to the coil #2 (340BH), the center line speed is increased to 135 mpm. In addition, at the time of a transition from the coil #2 (340BH) to the coil #3 (Nb—Ti sulc), the heating temperature is reduced to 480° C., and the center line speed is increased to 150 mpm.

During the on-line continuous measurement (the thick solid line in FIG. 11) of the present invention, the change in the thickness of the Γ·Γ$_1$ phase with the transition of the coils or the changes in the operational conditions is observed. For example, at the time of the transition from the coil #2 (340BH) to the coil #3 (Nb—Ti sulc) which is more easily alloyed, the thickness of the Γ·Γ$_1$ phase is discontinuously increased, and thereafter, by decreasing the heating temperature and increasing the line speed, the thickness of the Γ·Γ$_1$ phase is continuously reduced and then converges to an appropriate value. Contrary to this, during the on-line continuous measurement of the related art, the thickness of the Γ·Γ$_1$ phase fluctuates regardless of the operational changes.

Samples for evaluating the coating adhesion were collected from five places shown as Δ in FIG. 11. That is, the places are a tail portion (#1) of the coil 1, a front portion (#2-1) and a tail portion (#2-2) of the coil 2, and a front portion (#3-1) and a tail portion (#3-2) of the coil 3. Based on the operational evaluation conditions set in advance, #1 and #3-1 were disqualified, and #2-1, #2-2, #3-2 were qualified. When shipment is determined from the results, the coil #2 can be shipped. However, a part of the coil #3 cannot be shipped, and for the shipment, a shipping range thereof has to be determined by the U bead test while rewinding the coil #3 using a recoiling line and dividing the coil #3 into small coils. Contrary to this, when the on-line continuous measurement of the present invention is used, continuous determination is possible as shown in the low stage of FIG. 11, and thus a boundary position between OK and NG for shipment of the coil #3 is known. Therefore, the coil can be cut at an appropriate position and can be shipped immediately. Further, in the present invention, the results can be quickly fed back to the operational conditions, and thus the shipment NG range can be minimized. As a result, the yield is enhanced. Contrary to this, in the method according to the related art, such functions are not provided. Therefore, the X-ray diffraction on-line continuous measuring method of the present invention is significantly superior to the method according to the related art.

While the preferable embodiments of the present invention have been described in detail with reference to the drawings, the present invention is not limited to the embodiments. It should be noted by those skilled in the art to which the present invention belongs that various changes and modification examples can be made in the scope of the technical idea described in the appended claims, and these examples naturally belong to the technical range of the present invention.

INDUSTRIAL APPLICABILITY

According to the present invention, a galvannealed steel sheet with stable quality can be supplied at low cost, and thus the spread of vehicles with excellent antirust properties is further accelerated. This is connected to the enhancement in the life-span and safety of vehicles and contributes to the improvement in the global environment from the viewpoint of saving resources. Therefore, industrial utility is extremely high.

DESCRIPTION OF REFERENCE NUMERALS AND SIGNS

1: X-RAY TUBE (Cr)
2: DETECTOR ($\Gamma \cdot \Gamma_1$ PHASE PEAK DETECTOR)
3: DETECTOR (BACKGROUND DETECTOR: HIGH ANGLE SIDE)
4: DETECTOR (BACKGROUND DETECTOR: LOW ANGLE SIDE)
5: HEAD
6: STEEL STRIP
11: X-RAY TUBE (Cu)
12: DETECTOR ($\Gamma \cdot \Gamma_1$ PHASE PEAK DETECTOR)
13: DETECTOR (BACKGROUND DETECTOR: HIGH ANGLE SIDE)
14: DETECTOR (BACKGROUND DETECTOR: LOW ANGLE SIDE)
15: HEAD
16: STEEL STRIP
21: X-RAY TUBE (Cr)
22: DETECTOR ($\Gamma \cdot \Gamma_1$ PHASE PEAK DETECTOR)
23: DETECTOR ($\delta_1$ PHASE PEAK DETECTOR)
24: DETECTOR ($\zeta$ PHASE PEAK DETECTOR)
25: DETECTOR ($\Gamma \cdot \Gamma_1$ PHASE BACKGROUND DETECTOR: HIGH ANGLE SIDE)
26: DETECTOR ($\delta_1$ PHASE BACKGROUND DETECTOR: HIGH ANGLE SIDE)
27: DETECTOR ($\zeta$ PHASE BACKGROUND DETECTOR: HIGH ANGLE SIDE)
28: HEAD
29: STEEL STRIP

The invention claimed is:

1. A method of measuring a thickness of a Fe—Zn alloy phase of interest included in the Fe—Zn alloy phase of a galvannealed steel sheet, the method comprising:
    an X-ray irradiation process of irradiating the galvannealed steel sheet with the incident X-rays; and
    an X-ray detection process of detecting the diffracted X-rays, which are obtained in the X-ray irradiation process, derived from a $\Gamma \cdot \Gamma_1$ phase, a $\delta 1$ phase, and a $\zeta$ phase included in the Fe—Zn alloy phase with a crystal lattice spacing d of 1.5 Å or higher,
    wherein, in the X-ray detection process, a value obtained by subtracting a background intensity from an intensity of the diffracted X-ray with the crystal lattice spacing d corresponding to 1.507 Å, 1.536 Å, 1.623 Å, 1.720 Å, 1.833 Å, 1.899 Å, 1.914 Å, 1.971 Å, 2.363 Å, 2.593 Å, 2.770 Å, 3.692 Å, 4.109 Å, 5.535 Å, or 6.351 Å is used to measure the thickness of the Fe—Zn alloy phase of interest.

2. The method of measuring a thickness of a Fe—Zn alloy phase of the galvannealed steel sheet according to claim 1,
    wherein, in the X-ray detection process, a thickness of the $\Gamma \cdot \Gamma_1$ phase is measured using a value obtained by subtracting a background intensity from an intensity of the diffracted X-ray derived from the $\Gamma \cdot \Gamma_1$ phase with the crystal lattice spacing d of 1.914 Å.

3. The method of measuring a thickness of a Fe—Zn alloy phase of the galvannealed steel sheet according to claim 1 or 2,
    wherein, in the X-ray detection process, a thickness of the $\delta_1$ phase is measured using a value obtained by subtracting a background intensity from an intensity of the diffracted X-ray derived from the $\delta_1$ phase with the crystal lattice spacing d of 2.363 Å.

4. The method of measuring a thickness of a Fe—Zn alloy phase of the galvannealed steel sheet according to claim 1 or 2,
    wherein, in the X-ray detection process, a thickness of the $\zeta$ phase is measured using a value obtained by subtracting a background intensity from an intensity of the diffracted X-ray derived from the $\zeta$ phase with the crystal lattice spacing d of 4.109 Å.

5. An apparatus used to measure a thickness of a Fe—Zn alloy phase of a galvannealed steel sheet, the apparatus comprising:
    an X-ray tube; and
    a detector which detects diffracted X-rays from the Fe—Zn alloy phase to measure an intensity of the diffracted X-ray,
    wherein a diffraction angle between a direction of incident X-ray irradiated by the X-ray tube and a direction of the diffracted X-ray detected by the detector is an angle corresponding to a $\Gamma \cdot \Gamma_1$ phase, a $\delta_1$ phase, and a $\zeta$ phase included in the Fe—Zn alloy phase, and with a crystal lattice spacing d of 1.5 Å or higher, and wherein
    the diffraction angle is an angle that corresponds to the crystal lattice spacing d of 1.507 Å, 1.536 Å, 1.623 Å, 1.720 Å, 1.833 Å, 1.899 Å, 1.914 Å, 1.971 Å, 2.363 Å, 2.593 Å, 2.770 Å, 3.692 Å, 4.109 Å, 5.535 Å, or 6.351 Å.

6. The apparatus used to measure a thickness of a Fe—Zn alloy phase of the galvannealed steel sheet according to claim 5,
wherein the diffraction angle is an angle that corresponds to the crystal lattice spacing d of 1.914 Å.

7. The apparatus used to measure a thickness of a Fe—Zn alloy phase of the galvannealed steel sheet according to claim 5 or 6,
wherein the diffraction angle is an angle that corresponds to the crystal lattice spacing d of 2.363 Å.

8. The apparatus used to measure a thickness of a Fe—Zn alloy phase of the galvannealed steel sheet according to claim 5 or 6,
wherein the diffraction angle is an angle that corresponds to the crystal lattice spacing d of 4.109 Å.

9. The apparatus used to measure a thickness of a Fe—Zn alloy phase of the galvannealed steel sheet according to claim 5 or 6,
wherein two or more of the detectors are included, and
the diffracted X-rays derived from at least two phases among the $\Gamma \cdot \Gamma_1$ phase, the $\delta_1$ phase, and the $\zeta$ phase are detected by the detectors.

10. The method of measuring a thickness of a Fe—Zn alloy phase of the galvannealed steel sheet according to claim 3,
wherein, in the X-ray detection process, a thickness of the $\zeta$ phase is measured using a value obtained by subtracting a background intensity from an intensity of the diffracted X-ray derived from the $\zeta$ phase with the crystal lattice spacing d of 4.109 Å.

11. The apparatus used to measure a thickness of a Fe—Zn alloy phase of the galvannealed steel sheet according to claim 7,
wherein the diffraction angle is an angle that corresponds to the crystal lattice spacing d of 4.109 Å.

12. The apparatus used to measure a thickness of a Fe—Zn alloy phase of the galvannealed steel sheet according to claim 7,
wherein two or more of the detectors are included, and
the diffracted X-rays derived from at least two phases among the $\Gamma \cdot \Gamma_1$ phase, the $\delta_1$ phase, and the $\zeta$ phase are detected by the detectors.

13. The apparatus used to measure a thickness of a Fe—Zn alloy phase of the galvannealed steel sheet according to claim 8,
wherein two or more of the detectors are included, and
the diffracted X-rays derived from at least two phases among the $\Gamma \cdot \Gamma_1$ phase, the $\delta_1$ phase, and the $\zeta$ phase are detected by the detectors.

* * * * *